(12) United States Patent
Pruter

(10) Patent No.: US 7,635,336 B1
(45) Date of Patent: *Dec. 22, 2009

(54) METHOD AND APPARATUS FOR GUIDING NEEDLES

(76) Inventor: Rick L. Pruter, 21 Woodcrest La. NE., Iowa City, IA (US) 52240

( * ) Notice: Subject to any disclaimer, the term of this patent is extended or adjusted under 35 U.S.C. 154(b) by 460 days.

This patent is subject to a terminal disclaimer.

(21) Appl. No.: 11/423,283

(22) Filed: Jun. 9, 2006

Related U.S. Application Data

(63) Continuation of application No. 10/250,149, filed on Jun. 6, 2003, now Pat. No. 7,087,024, which is a continuation of application No. 09/682,367, filed on Aug. 24, 2001, now Pat. No. 6,612,990, which is a continuation-in-part of application No. 09/526,048, filed on Mar. 15, 2000, now Pat. No. 6,296,614, which is a continuation-in-part of application No. 29/103,098, filed on Apr. 8, 1999, now Pat. No. Des. 424,693.

(51) Int. Cl.
*A61B 8/14* (2006.01)
(52) U.S. Cl. .................................. 600/461
(58) Field of Classification Search ............ 600/437, 600/459, 461, 56, 471, 562; 606/130; 604/116
See application file for complete search history.

(56) References Cited

U.S. PATENT DOCUMENTS

| | | | |
|---|---|---|---|
| 2,451,183 A | 10/1948 | Tantimonaco | |
| 2,536,963 A | 1/1951 | Stephens | |
| 3,017,887 A | 1/1962 | Heyer | |
| 3,538,915 A | 11/1970 | Frampton et al. | |
| 3,556,079 A | 1/1971 | Omizo | |
| 3,924,138 A | 12/1975 | Duprez | |
| 4,029,084 A | 6/1977 | Soldner | |
| 4,058,114 A * | 11/1977 | Soldner | 600/461 |
| 4,108,165 A | 8/1978 | Kopp et al. | |
| 4,132,496 A | 1/1979 | Casto | |
| 4,249,539 A | 2/1981 | Vilkomerson et al. | |
| 4,289,139 A | 9/1981 | Enjoji et al. | |
| 4,332,248 A | 6/1982 | DeVitis | |
| 4,363,326 A | 12/1982 | Kopel | |
| 4,402,324 A | 9/1983 | Lindgren et al. | |
| 4,408,611 A | 10/1983 | Enjoji | |
| 4,414,908 A | 11/1983 | Eguchi et al. | |
| 4,469,106 A * | 9/1984 | Harui | 600/461 |
| 4,489,730 A | 12/1984 | Jingu | |
| 4,491,137 A | 1/1985 | Jingu | |

(Continued)

OTHER PUBLICATIONS

"ultrasoundsupplies.com" brochure of Civco Medical Instruments Co.

(Continued)

*Primary Examiner*—Long V Le
*Assistant Examiner*—Salieu M Abraham
(74) *Attorney, Agent, or Firm*—Simmons Perrine Moyer Bergman PLC

(57) ABSTRACT

An apparatus and method for guiding a needle in conjunction with a biopsy using a medical imaging device, where an open-ended needle guide with an adjustable slidable multi-gauge needle stop is used to guide a needle during insertion and during a tilting of the needle with respect to the medical imaging device.

20 Claims, 2 Drawing Sheets

U.S. PATENT DOCUMENTS

| | | | |
|---|---|---|---|
| 4,497,325 | A | 2/1985 | Wedel |
| 4,504,269 | A | 3/1985 | Durand |
| 4,542,747 | A | 9/1985 | Zurinski et al. |
| 4,608,989 | A * | 9/1986 | Drue .......................... 600/461 |
| 4,635,644 | A * | 1/1987 | Yagata ....................... 600/464 |
| 4,773,288 | A | 9/1988 | Jang et al. |
| 4,781,067 | A | 11/1988 | Cichanski |
| 4,838,506 | A * | 6/1989 | Cooper ....................... 248/200 |
| 4,898,178 | A | 2/1990 | Wedel |
| 4,899,756 | A | 2/1990 | Sonek |
| 4,970,907 | A | 11/1990 | Flynn |
| 5,052,396 | A * | 10/1991 | Wedel et al. ................ 600/461 |
| 5,076,279 | A * | 12/1991 | Arenson et al. ............ 600/461 |
| 5,088,500 | A | 2/1992 | Wedel et al. |
| 5,161,764 | A | 11/1992 | Roney |
| 5,235,987 | A * | 8/1993 | Wolfe ......................... 600/461 |
| 5,300,082 | A | 4/1994 | Sharpe et al. |
| 5,343,865 | A | 9/1994 | Gardineer et al. |
| D362,064 | S | 9/1995 | Smick |
| 5,623,931 | A * | 4/1997 | Wung et al. ................. 600/461 |
| D383,968 | S | 9/1997 | Bidwell et al. |
| 5,758,650 | A * | 6/1998 | Miller et al. ................ 600/461 |
| 5,871,448 | A | 2/1999 | Ellard |
| 5,910,113 | A | 6/1999 | Pruter |
| 5,911,707 | A * | 6/1999 | Wolvek et al. .............. 604/116 |
| 5,924,992 | A | 7/1999 | Park et al. |
| 5,941,889 | A * | 8/1999 | Cermak ....................... 606/130 |
| D424,693 | S | 5/2000 | Pruter |
| 6,095,981 | A | 8/2000 | McGahan |
| 6,139,544 | A | 10/2000 | Mikus et al. |
| 6,203,499 | B1 * | 3/2001 | Imling et al. ................ 600/461 |
| 6,296,614 | B1 | 10/2001 | Pruter |
| 6,311,084 | B1 | 10/2001 | Cormack et al. |
| 6,379,307 | B1 * | 4/2002 | Filly et al. .................. 600/461 |
| 6,475,152 | B1 * | 11/2002 | Kelly et al. ................. 600/461 |
| 6,612,990 | B1 | 9/2003 | Pruter |
| 6,695,786 | B2 * | 2/2004 | Wang et al. ................. 600/461 |
| 7,022,082 | B2 * | 4/2006 | Sonek ......................... 600/461 |
| 7,241,267 | B2 * | 7/2007 | Furia .......................... 600/461 |
| 7,322,990 | B1 * | 1/2008 | Mark et al. ................. 606/130 |

OTHER PUBLICATIONS

"Endocavity Needle Guide Kits" brochure of Civco Medical Instruments, © 2000, Solutions for Imaging.

"General Purpose Needle Guides and Transducer Covers" brochure of Civco Medical Instruments, Sonosite Cross-Reference Information.

"Needle Guidance Systems, Transducer Covers, GE Medical Systems", gemedicalsystems.com brochure of Civco Medical Instruments, Solutions for Imaging.

UltraGuide 1000 System 4-page brochure, UltraGuide Ltd., Tirat Hacarmel Industrial Park, P O Box 2070, Tirat Hacarmel 30200, Israel.

UltraGuide 1000 2-page brochure, UltraGuide Ltd., Tirat Hacarmel Industrial Park, P O Box 2070, Tirat Hacarmel 30200, Israel.

"Civcoscan, Product News and Special Offers From Civco" Brochure of Civco Medical instruments, Winter 2001.

Solutions for Ultrasound, Civco Medical Instruments Co., Inc., Medical Parkway, 102 Highway 1 South, Kalona, IA 52247.

Program for Medical Ultrasound Professionals, Winter 1995, Civco Medical Instrument Co., Inc., Medical Parkway, 102 Highway 1 South, Kalona, IA 52247.

Disposable Transrectal Needle Guide, Civco Medical Instruments Co., Inc., Medical Parkway, 102 Highway 1 South, Kalona, IA 52247.

Maggi & Maggi II Plus, Sterile General Purpose Biopsy Needle Guides, Civco Medical Instrument Co., Inc., Medical Parkway, 102 Highway 1 South, Kalona, IA 52247.

Ultra-Pro Sterile General Purpose Biopsy Needle Guide, Civco Medical Instruments Co., Inc., Medical Parkway, 102 Highway 1 South, Kalona, IA 52247.

Aloka Needle Guide/Probe Cover Kits, Civco Medical Instruments Co., Inc., Medical Parkway, 102 Highway 1 South, Kalona, IA 52247.

Multi Pro 2000, Multi-Purpose Ultrasound Linear Tracking Instrument, Civco Medical instruments Co., Inc., 418 B Avenue, Kalona, IA 52247.

"The Ultimate Guide in Ultrasound" advertising, Civco Medical Instruments Co., Inc., 418 B Avenue, Kalona, IA 52247.

"Hitting the Mark with Realtime Guidance", Civco PROgram, Drawer Q, Kalona, IA 52247.

"Dedicated Breast Ultrasound, USI Introduces A Revolution In Breast Ultrasound . . . Vista" by USI The Breast Imaging Company. Three-page web page of amedic.se printed on Nov. 5, 2002.

Affidavit dated Jun. 27, 2003 of Applicant Admitted Prior Art.

"ultrasoundsupplies.com" brochure of Civco Medical Instruments Co.

"Endocavity Needle Guide Kits" brochure of Civco Medical Instruments, © 2000, Solutions for Imaging.

"General Purpose Needle Guides and Transducer Covers" brochure of Civco Medical instruments, Sonosite Cross-Reference Information.

"Needle Guidance Systems, Transducer Covers, GE Medical Systems", gemedicalsystems.com brochure of Civco Medical Instruments, Solutions for Imaging.

UltraGuide 1000 System 4-page brochure, Guide Ltd., Tirat Hacarmel Industrial Park, P O Box 2070, Tirat Hacarmel 30200, Israel.

UltraGuide 1000 2-page brochure, UltraGuide Ltd., Tirat Hacarmel Industrial Park, P O Box 2070, Tirat Hacarmel 30200, Israel.

"Civcoscan, Product News and Special Offers From Civco" Brochure of Civco Medical Instruments, Winter 2001.

Solutions for Ultrasound, Civco Medical Instruments Co., Inc., Medical Parkway, 102 Highway 1 South, Kalona, IA 52247.

Program for Medical Ultrasound Professionals, Winter 1995, Civco Medical Instrument Co., Inc., Medical Parkway, 102 Highway 1 South, Kalona, IA 52247.

Disposable Transrectal Guide, Civco Medical Instruments Co., Inc., Medical Parkway, 102 Highway 1 South, Kalona, IA 52247.

Maggi & Maggi ll Plus. Sterile General Purpose Biopsy Needle Guides, Civco Medical Instrument Co., Inc., Medical Parkway, 102 Highway 1 South, Kalona, IA 52247.

Ultra-Pro Sterile General Purpose Biopsy Needle Guide, Civco Medical Instruments Co., Inc., Medical Parkway, 102 Highway 1 South, Kalona, IA 52247.

Aloka Needle Guide/Probe Cover Kits, Civco Medical Instruments Co., Inc., Medical Parkway, 102 Highway 1 South, Kalona, IA 52247.

Multi Pro 2000, Multi-Purpose Ultrasound Linear Tracking Instrument, Civco Medical Instruments Co., Inc., 418 B Avenue, Kalona, IA 52247.

"The Ultimate Guide in Ultrasound" advertising, Civco Medical Instruments Co., Inc., 418 B Avenue, Kalona, IA 52247.

"Hitting the Mark with Realtime Guidance", Civco PROgram, Drawer Q, Kalona, IA 52247.

"Dedicated Breast Ultrasound, USI Introduces A Revolution In Breast Ultrasound . . . Vista" by USI The Breast Imaging Company. Three-page web page of amedic.se printed on Nov. 5, 2002.

Affidavit dated Jun. 27, 2003 of Applicant Admitted Prior Art.

* cited by examiner

METHOD AND APPARATUS FOR GUIDING NEEDLES

CROSS-REFERENCE TO RELATED APPLICATIONS

The present application is a continuation of co-pending application Ser. No. 10/250,149 entitled "Method and apparatus for guiding needles" filed by the same inventor on Jun. 6, 2003, which is a continuation of application Ser. No. 09/682,367 entitled "Method and apparatus for guiding needles", filed by the same inventor on Aug. 24, 2001, which application issued as U.S. Pat. No. 6,612,990 B1 on Sep. 2, 2003, and which itself was a continuation-in-part application of an application entitled "Needle guide for attachment to ultrasound transducer probe" by the same inventor, the application having Ser. No. 09/526,048 which was filed on Mar. 15, 2000, and issued as U.S. Pat. No. 6,296,614 on Oct. 2, 2001, which itself was a continuation-in-part of application Ser. No. 29/103,098, also entitled "Needle guide for attachment to ultrasound transducer probe" filed on Apr. 8, 1999, which issued as U.S. Pat. No. Des. 424,693 on May 9, 2000. The above-referenced application, Patents and U.S. Design Patent are incorporated herein in their entirety by these references.

FIELD OF THE INVENTION

The present invention generally relates to needle guides for medical imaging transceivers, and more particularly relates to needle guides for medical imaging transceivers which permit tipping of a needle while still in the needle guide.

BACKGROUND OF THE INVENTION

In recent years, handheld medical imaging transceivers, such as ultrasound and gamma ray transceivers, have been used extensively for various medical imaging situations. In certain procedures, such as biopsies, it may be desired to tilt a needle with respect to a needle guide or vice versa.

In the past, the physician or medical professional may be required to detach a biopsy needle from a needle guide prior to changing the angle of the needle with respect to the needle guide and transceiver. Other prior art needle guides have included a pair of spaced-apart fixed parallel plates. The medical professional could place the needle between the parallel plates, and it would be free in a plane parallel with the plates, but restricted from large movements outside that plane.

Other prior art needle guides have been used which include a resilient tube coupled to a transducer where the tube has a longitudinal slit through which the needle can be pulled when relative tilting is required.

While these needle guides have been used extensively in the past, they do have some drawbacks. First of all any model of fixed parallel plate needle guide is limited in the size of needle that can be guided therein. If the needle is too big, it will not fit between the fixed parallel plates. If the plates are too far apart, there is less support being provided in the desired direction. Also, these parallel plate needle guides only provide support in one direction. They provide no support or resistance from motion within the plane of the parallel gap between the fixed plates. This increases the attention required by the medical professional.

Secondly, the resilient slit tube type of needle guide does provide some resistance to motion in the desired plane of motion, but it is limited to only the first portion of that movement or motion. Once the needle is tilted out of the tube, there is no support or resistance to motion in any direction. Additionally, these types of needle guides will work only with specific gauges of needles. They will not work well when a narrow gauge needle is used in a needle guide primarily designed for a larger needle. The narrower needle may fall through the slit. Conversely, a larger needle may not fit in the tube, or it may be difficult to pull through the slit. Consequently, numerous sized slit tube needle guides would be needed to fulfill the needs of a medical professional who uses needles of varying sizes. Additionally, these slit tube type of needle guides may be viewed as unstable in the direction of relative motion. For example, the force required to be applied to the needle to move the needle in the tilted direction decreases as the amount of tilting occurs. To assure that excess tilting does not occur, the medical professional needs to give more attention to the force being applied when the required force decreases with angular displacement.

Consequently, there exists a need for improved methods and apparatus for guiding needles in an efficient manner.

SUMMARY OF THE INVENTION

It is an object of the present invention to provide an apparatus and method for guiding a tiltable needle in an efficient manner.

It is a feature of the present invention to utilize a multi-gauge adjustable needle guide.

It is another feature of the present invention to include a slidable needle stop.

It is another feature of the present invention to include a slide-ably adjustable needle guide stop with a bias force for closing the needle guide.

It is another feature of the present invention to include needle stops having contours for engaging needles.

It is an advantage of the present invention to achieve improved efficiency in guiding needles.

The present invention is an apparatus and method for guiding needles designed to satisfy the aforementioned needs, provide the previously stated objects, include the above-listed features, and achieve the already articulated advantages. The present invention is carried out in a "physician burden-less" manner in a sense that the burden on a physician or other medical professional in guiding needles during the process of tilting has been greatly reduced.

Accordingly, the present invention is an apparatus and method including a slidable needle stop in a multi-gauge adjustable needle guide.

BRIEF DESCRIPTION OF THE DRAWINGS

The invention may be more fully understood by reading the following description of the preferred embodiments of the invention, in conjunction with the appended drawings wherein.

DETAILED DESCRIPTION

Figure 1:
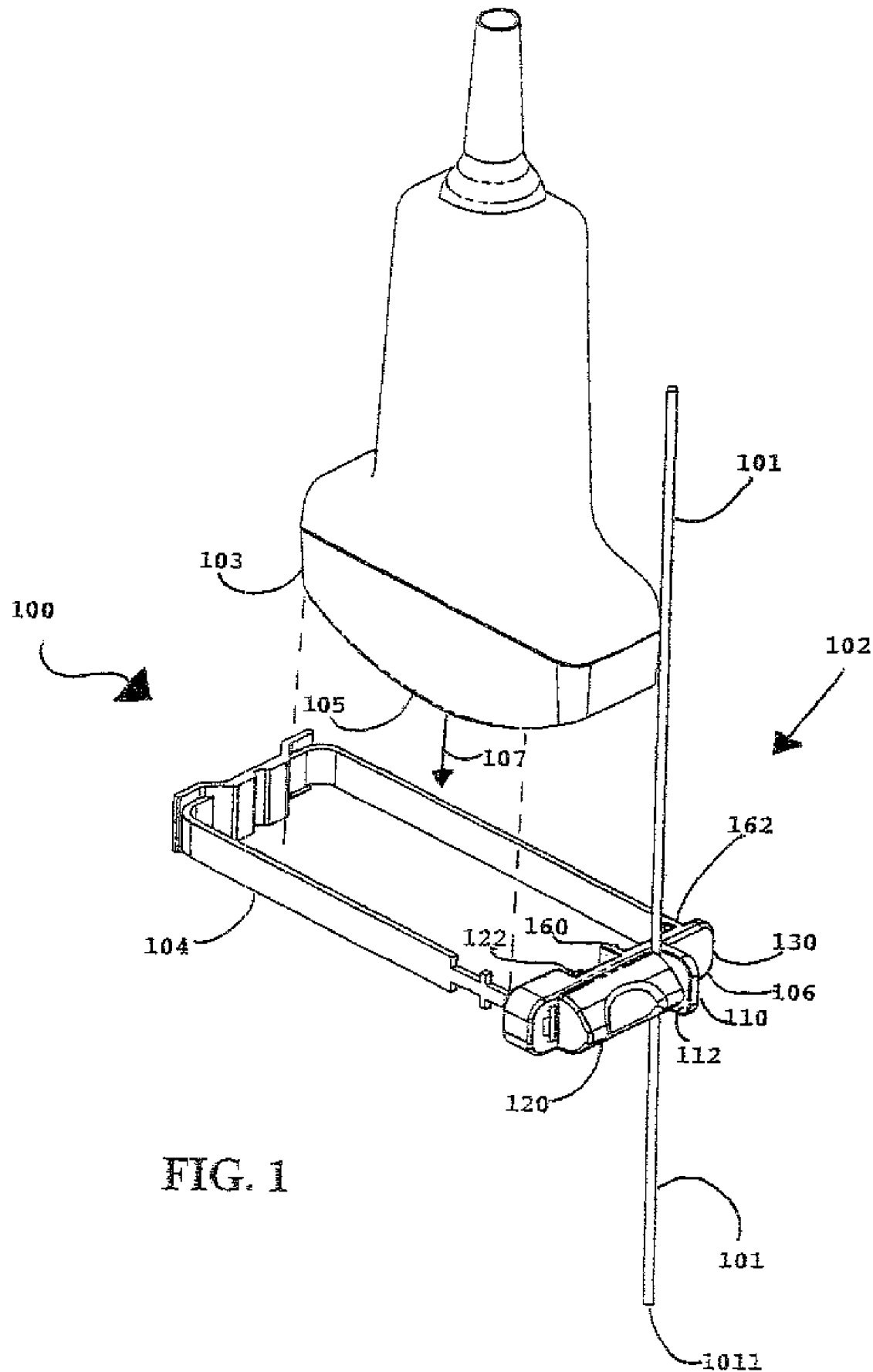
FIG. 1 is a partially exploded perspective view of the apparatus of the present invention.

Now referring to the drawings wherein like numerals refer to like matter throughout, and more specifically referring to FIG. 1, there is shown a needle guide assembly 100, of the present invention which includes a needle guide 102 with a needle 101 disposed therein. Needle guide 102 is coupled to medical imaging device 103, which could be an ultrasound transducer, gamma ray transceiver or other imaging device, via a medical imaging device retaining strap 104, which could be an elastic strap, such as rubber or a less elastic strap, such as fabric or leather. Cables, wires, rope, brackets, clamps or any other suitable substitute could be used for a medical imaging device retaining strap 104. Needle guide 102 is preferably a plastic material, such as ABS or equivalent; however, other materials, such as aluminum, surgical steel, and any other suitable material could be substituted.

The medical imaging device 103 has a transmitting end 105, which may be a planar face with a vertical axis 107 extending orthogonally therefrom.

The term "vertical axis 107" is used herein to convey that the axis is orthogonal to the transmitting surface end 105. Depending on the orientation of the medical imaging device 103, the vertical axis 107 may be pointed in any direction with respect to the patient or an earth reference in normal operation, the medical imaging device 103 is often held, at least at first, with the transmitting end 105 in a substantially horizontal (earth reference) arrangement. This arrangement results in the vertical axis 107 being orientated in a vertical (earth reference) direction.

Needle guide 102 has a slidable needle stop 120 which may be contoured on its top side to facilitate engagement with a human finger or thumb. Slidable needle stop 120 is preferably slidable along needle guide main body 106 which contains a first needle stop 110. However, other arrangements between the slidable needle stop 120 and first needle stop 110 could be substituted. First needle stop 110 may be vertical and have a planar needle engagement surface 112 as shown, but other arrangements could be employed as well.

Also shown in FIG. 1 are members 160 and 162, which can form a pliable clip for attaching needle guide 102 to a bracket (not shown) coupled to a medical imaging transceiver when strap 104 is not used.

Figure 2:
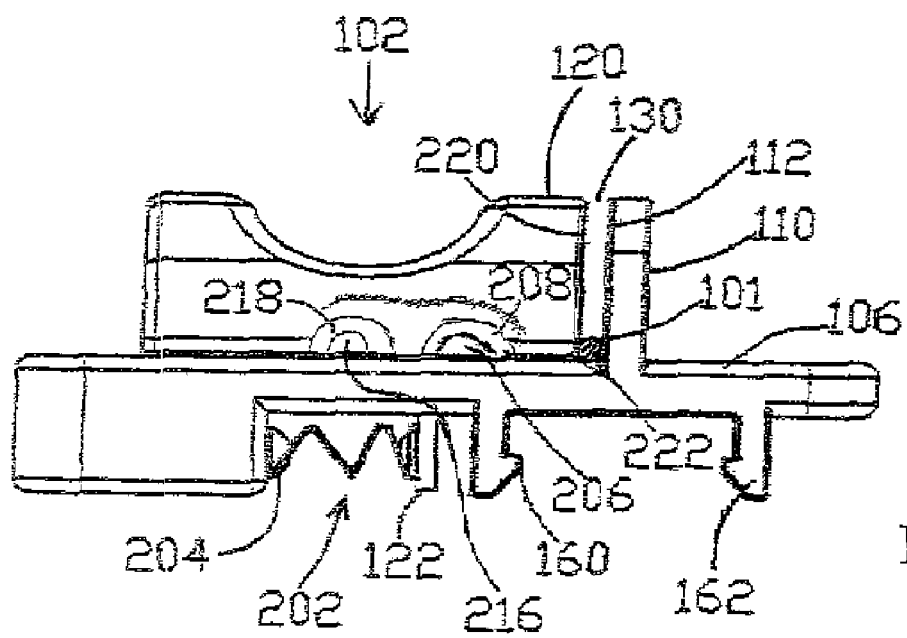
FIG. 2 is an enlarged partially cut-away side view of the needle guide of FIG. 1, where the cut-away portion exposes a plurality of detent mechanisms.

Now referring to FIG. 2, there is shown a partially cut-away side view of the needle guide 102 of FIG. 1. Needle guide 102 is shown having a spring 202, which could be a simple metal or plastic spring, or it could be any resilient member or other apparatus capable of biasing sliding spring stop 122 so as to tend to minimize the width of needle gap 130. Spring 202 is shown disposed between fixed spring stop 204 and sliding spring stop 122. Needle guide 102 is also shown in the cut-away portion as having a needle guide main body 106, first detent protrusion 206 and second detent protrusion 216 which are received by first detent protrusion receiving void 208 and second detent protrusion receiving void 218 both found in slidable needle stop 120. Slidable needle stop 120 is shown having a top leading edge 220 and a bottom angled leading edge 222. Preferably, the pressure exerted by spring 202 is sufficient to hold needle 101 stationary unless a force other than gravity acts upon it.

Figure 3:
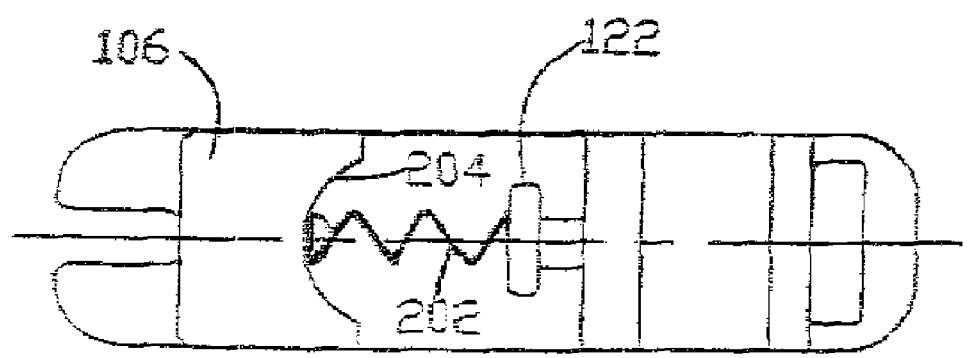
FIG. 3 is a bottom view of the needle guide of FIGS. 1 and 2.

Now referring to FIG. 3, there is shown a bottom view of the needle guide 102 of FIGS. 1 and 2.

In operation, the apparatus and method of the present invention as described and shown in FIGS. 1-3, could function as follows:

Needle guide 102 is attached to medical imaging device 103 via medical imaging device retaining strap 104. The needle guide 102 is readied for receipt of the needle 101 by sliding slidable needle stop 120 to create a gap sufficiently large to accommodate the particular biopsy needle used. The biopsy needle, such as needle 101, is inserted into needle gap 130 and slidable needle stop 120 is released, thereby holding needle 101. The needle 101 is then inserted into the patient. Medical imaging device 103 is used to create a first image of a portion of a human body. The medical imaging device 103 and needle guide 102 are then tilted with respect to the needle 101. This provides a different angle of view of the end 1011 of the needle 101. A second image is then created by the medical imaging device 103. The needle may be held stationary and the medical imaging device 103 and needle guide 102 tilted, or vice versa.

The tilting of the needle 101 or needle guide 102 is done by applying a force between the two. As the angle of separation between the vertical axis 107 and the longitudinal axis of the needle 101 increases, the amount of contact between the needle 101 and planar needle engagement surface 112 and top leading edge 220 increases. This increases the friction on the needle 101 thereby increasing the force needed to move the needle 101 to larger angular separations with respect to the needle guide 102.

Throughout this description, reference is made to a medical imaging system, because it is believed that the beneficial aspects of the present invention would be most readily apparent when used in connection with medical imaging; however, it should be understood that the present invention is not intended to be limited to imaging, and should be hereby construed to include other medical tools, equipment and methodologies as well, where it is desirable to guide a needle.

Throughout this document, references are made to "vertical" and "horizontal". These terms are intended to mean "substantially vertical" and "substantially horizontal". Minor deviations from vertical and minor deviations from horizontal are intended to be included therein. Also see the above definition on vertical axis 107.

It is thought that the method and apparatus of the present invention will be understood from the foregoing description and that it will be apparent that various changes may be made in the form, construct steps, and arrangement of the parts and steps thereof, without departing from the spirit and scope of the invention or sacrificing all of their material advantages. The form herein described is merely a preferred exemplary embodiment thereof.

I claim:

1. A needle guide apparatus comprising:
   an elongated flexible strap, having a longitudinal strap axis, which is configured for wrapping, so as to provide for continuous contact with contiguous curved surfaces, in a substantially horizontal direction, at least partially around an exterior of a medical imaging transceiver, having a substantially vertical axis, a bottom transmitting surface and an opposing top end;
   said elongated flexible strap being in continuous contact with and conformable to predetermined varied shapes of sections of medical imaging transceivers;
   said elongated flexible strap being elastic along the longitudinal strap axis;
   a member coupled to and receiving support from said elongated flexible strap;
   said member and said elongated flexible strap coupled, in series, to encircle a portion of said medical imaging transceiver, without passing over the top end or under the bottom transmitting surface;
   means for retaining an end of said elongated flexible strap;
   said member further comprising structure which is configured to guide a needle and further configured to limit, in at least one direction, movement of the needle.

2. A needle guide apparatus of claim 1 wherein said portion of said medical imaging transceiver is free from any recesses therein wherein sides of the recesses provide support of the member.

3. A needle guide apparatus of claim 1 wherein said portion of said medical imaging transceiver is continuously convex in shape along the longitudinal strap axis.

4. A needle guide apparatus of claim 1 wherein said portion of said medical imaging transceiver has an external surface which provides support only along a line which is orthogonal to both the longitudinal strap axis and the vertical axis.

5. A needle guide apparatus of claim 1 wherein the member is not disposed between any transmitting surfaces of the medical imaging transceiver.

6. A needle guide apparatus of claim 1 wherein the member is configured to receive thereon a structure comprising a movable needle stop.

7. A needle guide apparatus of claim 6 wherein the movable needle stop is movable with respect to a first needle stop.

8. A needle guide apparatus of claim 7 wherein the first needle stop is rigidly coupled to the member.

9. The needle guide apparatus of claim 8 wherein the first needle stop is integrally formed on the member.

10. The needle guide apparatus of claim 7 wherein the structure is detachable from the member.

11. A system for guiding a needle comprising:
a medical imaging transceiver, configured to generate signals representative of an internal portion of a human body;
a first needle stop having a first needle engagement surface;
a movable needle stop having a movable stop surface opposing said needle engagement surface so as to form a needle gap therebetween;
said movable needle stop being movable so as to change a needle gap dimension; and
an elongated flexible strap being elastic along a longitudinal axis, further being conformable so as to wrap around at least a portion of the medical imaging transceivers so as to provide for continuous contact with contiguous curved surfaces, and further configured to aid in providing a retaining force for biasing the first needle stop toward a portion of the medical imaging transceiver,
WHEREBY said first needle stop and said movable needle stop are configured to cooperate to provide needle engaging forces upon a needle when said needle is disposed in said needle gap and simultaneously configured to permit removal of said needle from said needle gap, and the first needle stop and the movable needle stop are biased toward the medical imaging transceiver by at least the elongated flexible strap.

12. A system of claim 11 wherein said first needle stop is rigidly coupled to a member coupled to the elongated flexible strap.

13. A system of claim 11 wherein said first needle stop and said movable needle stop provide for an ability of tilting of a needle out of a needle guide formed by the first needle stop and said movable needle stop without removing the needle from a patient.

14. A system of claim 11 wherein said movable needle stop is biased by a flexible member so as to reduce said needle gap dimension.

15. A system of claim 14 wherein said flexible member is a spring.

16. A system of claim 11 wherein said movable needle stop is configured for non-pivotal motion with respect to said first needle stop.

17. A system of claim 16 wherein said non-pivotal motion is a sliding motion.

18. A system of claim 12 wherein said first needle stop is permanently coupled to the member.

19. A system of claim 12 wherein said movable needle stop is detachable from the member.

20. A needle guide comprising:
a medical imaging transceiver;
a first needle stop, having a first needle engagement surface;
a second needle stop having a second needle engagement surface;
a needle receiving gap formed by said first needle receiving surface and said second needle receiving surface;
said second needle stop being movable with respect to said first needle stop, and said needle receiving gap having a variable needle gap dimension in response to movement of said second needle stop;
a rigid member, wherein said first needle stop is configured to be capable of a rigid connection with the member and the second needle stop is configured to be capable of an adjustable connection; and
an elastic belt configured to wrap, in a substantially horizontal direction, around a portion of the medical imaging transceiver so as to provide for continuous contact with contiguous curved surfaces, and to hold a rigid member at a fixed location with respect to the medical imaging transceiver.

* * * * *